United States Patent
Lopez et al.

(10) Patent No.: US 10,531,659 B2
(45) Date of Patent: Jan. 14, 2020

(54) DISPERSIBLE HERBICIDAL COMPOSITIONS AND METHODS OF USE

(71) Applicant: AMVAC CHEMICAL CORPORATION, Newport Beach, CA (US)

(72) Inventors: Humberto Benito Lopez, Chino Hills, CA (US); Peter J. Porpiglia, Putnam Valley, NY (US)

(73) Assignee: AMVAC CHEMICAL CORPORATION, Amvac, CA (US)

( * ) Notice: Subject to any disclaimer, the term of this patent is extended or adjusted under 35 U.S.C. 154(b) by 0 days.

(21) Appl. No.: 16/389,571

(22) Filed: Apr. 19, 2019

(65) Prior Publication Data

US 2019/0239504 A1 Aug. 8, 2019

Related U.S. Application Data

(62) Division of application No. 13/950,604, filed on Jul. 25, 2013.

(60) Provisional application No. 61/741,819, filed on Jul. 25, 2012.

(51) Int. Cl.
    *A01N 25/04* (2006.01)
    *A01N 43/80* (2006.01)
    *A01N 41/10* (2006.01)

(52) U.S. Cl.
    CPC .............. *A01N 25/04* (2013.01); *A01N 41/10* (2013.01); *A01N 43/80* (2013.01)

(58) Field of Classification Search
    CPC combination set(s) only.
    See application file for complete search history.

(56) References Cited

U.S. PATENT DOCUMENTS

| | | |
|---|---|---|
| 5,000,775 A | 3/1991 | Grabiak et al. |
| 5,162,537 A | 11/1992 | Branningan et al. |
| 5,201,933 A | 4/1993 | Miller et al. |
| 5,225,570 A | 7/1993 | Williams et al. |
| 5,256,625 A | 10/1993 | Bussler et al. |
| 5,256,626 A | 10/1993 | Williams et al. |
| 5,256,630 A | 10/1993 | Bussler |
| 5,270,041 A | 12/1993 | Eugster et al. |
| 5,424,276 A | 6/1995 | Cain et al. |
| 5,484,760 A | 1/1996 | Bussler et al. |
| 5,502,025 A | 3/1996 | Bussler |
| 5,502,224 A | 3/1996 | Eugster et al. |
| 5,536,504 A | 7/1996 | Eugster et al. |
| 5,593,691 A | 1/1997 | Eugster et al. |
| 5,627,131 A | 5/1997 | Shribbs et al. |
| 5,710,100 A | 1/1998 | Bussler et al. |
| 5,880,066 A | 3/1999 | Wells et al. |
| 6,248,693 B1 | 6/2001 | Shribbs et al. |
| 2002/0106712 A1 | 8/2002 | Kloti et al. |
| 2006/0240984 A1 | 10/2006 | Pallett et al. |
| 2008/0300139 A1 | 12/2008 | Zawierucha et al. |
| 2009/0181850 A1 | 7/2009 | Stern et al. |
| 2010/0197502 A1 | 8/2010 | Gebhardt et al. |
| 2012/0021909 A1 | 1/2012 | Mathews et al. |
| 2012/0040826 A1 | 2/2012 | Jeanmart et al. |

FOREIGN PATENT DOCUMENTS

| | | | |
|---|---|---|---|
| WO | 2002090596 A1 | | 11/2002 |
| WO | 2009064703 A2 | | 5/2009 |
| WO | WO 2009/064703 | * | 5/2009 |
| WO | WO 2014/018775 | * | 1/2014 |

OTHER PUBLICATIONS

Manual on development and use of FAO and WHO specifications for pesticides, 1st ed., FAO Plant Production and Protection Paper 173, World Health Organization and Food and Agriculture Organization of the United Nations, 2002, section 7.12.*

Patent Cooperation Treaty, International Search Report for PCT/US2013/052096, dated Dec. 30, 2013, pp. 1-2.

* cited by examiner

*Primary Examiner* — John Pak
(74) *Attorney, Agent, or Firm* — Pillsbury Winthrop Shaw Pittman LLP

(57) ABSTRACT

Herbicidal dispersible concentrates include an herbicide and substantially water miscible amide-based solvents. Such concentrates may be diluted in water and used in methods to control weeds.

7 Claims, No Drawings

DISPERSIBLE HERBICIDAL COMPOSITIONS AND METHODS OF USE

STATEMENT OF RELATED APPLICATIONS

This application is a divisional of U.S. application Ser. No. 13/950,604, filed Jul. 25, 2013, which claims priority to U.S. Provisional Application No. 61/741,819 filed Jul. 25, 2012, the contents of which are incorporated herein by reference in their entirety.

BACKGROUND

Embodiments disclosed herein generally relate to herbicidal compositions and methods of using the same. More particularly, embodiments disclosed herein relate to dispersible compositions that facilitate dissolution of herbicidal active ingredients for efficient application.

Herbicides have enjoyed widespread use in commercial agriculture and have enabled an increase in crop yields and product quality. They are routinely used to control various weeds, for example, grasses and broadleaved weeds such as amaranthus, foxtails and others, whenever these weeds pose risks to crop yield.

Topramezone is an exemplary herbicide with a favorable herbicidal activity profile. It, like related herbicides with similar solubility profiles, is often formulated as a water dispersible granule (WG) or as a suspension concentrate (SC), i.e., a solid suspension. In such formulations, the active ingredients may be milled to a particular size and the solid subsequently suspended in an aqueous-based carrier vehicle. The WG formulation is typically made with inert compounds that have little adjuvancy and it can be difficult to make the active ingredient bioavailable to control weeds. Particulate size of the active ingredient in these formulations, and during application, often remains too large such that a substantial amount of the formulation has to be applied per acre to control weeds.

Similarly, a suspension concentrate formulation has the disadvantage that adjuvants are hard to incorporate at a useful rate and they provide little impetus for foliar uptake and biotranslocation, and thus a substantial amount of the formulation has to be applied per acre to control weed infestations.

SUMMARY

In some aspects, embodiments disclosed herein provide dispersible concentrates comprising about 0.1% to about 40% by weight of the concentrate of a methylsulfonylphenyl ketone herbicide and about 0.6% to about 90% by weight of the concentrate of a water-miscible amide solvent.

In some aspects, embodiments disclosed herein provide dispersible concentrates comprising about 0.1% to about 40% by weight of the concentrate of topramezone and about 0.6% to about 90% by weight of the concentrate of N-methyl pyrrolidone.

In some aspects, embodiments disclosed herein provide formulations comprising a dispersible concentrate and water, the dispersible concentrate comprising about 0.1% to about 40% by weight of the concentrate of a methylsulfonylphenyl ketone herbicide and about 0.6% to about 90% by weight of the concentrate of N-methyl pyrrolidone, wherein a ratio of dispersible concentrate to water is in a range from about 1:50 to 1:25,000 by volume, and wherein the formulation is in the form of a colloidal suspension.

In some aspects, embodiments disclosed herein provide methods of treating weeds comprising applying to the weeds an herbicidally effective amount of a formulation comprising a dispersible concentrate and water, the dispersible concentrate comprising about 0.1% to about 40% by weight of the concentrate of a methylsulfonylphenyl ketone herbicide and about 0.6% to about 90% by weight of the concentrate of N-methyl pyrrolidone, wherein in a ratio of dispersible concentrate to water is in a range from about 1:50 to 1:25,000 by volume, and wherein the formulation is in the form of a colloidal suspension.

DETAILED DESCRIPTION

Embodiments disclosed herein provide dispersible concentrates comprising about 0.1% to about 40% by weight of the concentrate of a methylsulfonylphenyl ketone herbicides and about 0.6% to about 90% by weight of the concentrate of a water-miscible amide solvent. In particular embodiments, the water miscible solvent is N-methyl pyrrolidone. N-methyl pyrrolidone (NMP) is a cyclic amide-based polar aprotic solvent that is substantially miscible with water in most any ratio. When an NMP solution containing an organic compound goes into water, NMP may immediately dissolve into the water phase and the organic compound may begin to precipitate or separate into a second liquid phase. If the organic compound of interest is an active herbicidal agent that separates rapidly, either the particle size may be difficult to control or the phase separation may render water-based application of the herbicide ineffective due to lack of solubility in water.

In the case of topramezone, and other methylphenylsulfonyl ketone herbicides disclosed herein, it has been discovered that their highly pH-dependent water solubility profiles (typically low below the $pK_a$ and fairly high above the $pK_a$) is compatible with, and even desirable for preparing amide-based concentrates, such as NMP concentrates. Such concentrates can be readily diluted with water to provide a colloidal suspension ideal for the treatment of weeds. Without being bound by theory, amide-based solvents may serve a dual role in successfully preparing the colloidal formulations disclosed herein: (1) amide-based solvents generally quickly solubilize methylphenylsulfonyl ketone herbicides in a shelf-stable concentrate and (2) amide-based solvents may provide a sufficient increase in operational pH after water dilution to prevent crystallization. By contrast, current suspension concentrates of these herbicides are manufactured at a pH below their $pK_a$ to avoid crystal growth during storage. When they are diluted the pH is low and the material is poorly solubilized and sprayed predominantly as a solid rather than a solution. As disclosed herein, the colloidal formulations prepared from amide-based dispersible concentrates demonstrate improved efficacy in the treatment of weeds in field trials. As used herein, "colloidal suspension" or "colloidal formulation" is distinguished from the coarse granule suspensions employed in the art in that the particle size is generally smaller in the colloidal system. In embodiments, the coarse granules of commercially available tompramezone, for example, may be greater than about 1 micron, or greater than about 5 microns, or greater than about 10 microns. By contrast, the colloidal formulations disclosed herein may be less than about 1 micron in size. This smaller particle size confers greater water solubility to the active ingredient, which ultimately provides greater delivery efficiency in the field.

One skilled in the art will appreciate that the principles that govern the successful use of NMP, as demonstrated in the Examples below, as the solvent vehicle for the dispersible concentrate may be obtained with similar polar aprotic solvents. Thus, other amide-based solvents that are highly miscible with water may be employed, including, without limitation, N,N-dimethylformamide (DMF), N,N-dimethylacetamide, formamide, N-methylformamide, and the like. Any amide-based solvent may be useful due to their ability to provide a slight increase in pH in water. In embodiments, other polar protic solvents may also be useful, albeit, with a lesser influence on pH. Thus, in embodiments, solvents such as dimethyl sulfoxide (DMSO), sulfolane, tetrahydrofuran (THF), and similar polar aprotic solvents may be useful. In embodiments, polar aprotic solvents may be selected for use in generating concentrates based on environmental and/or biocompatibility. In this regards, N-methyl pyrrolidone is particularly suitable.

Other solvents, co-solvents and/or additives (in any amount) that may be present in the concentrates or formulations disclosed herein include, without limitation, 1,3-Propanediol (CAS Reg. No. 504-63-2), 2-Ethyl-1-hexanol (CAS Reg. No. 104-76-7), 2-Ethylhexanol, 2-methyl-1,3-propanediol (CAS Reg. No. 2163-42-0), 2-Methyl-2,4-pentanediol, Acetic anhydride, Acetone (Cas Reg. No. 67-64-1), Ammonium hydroxide, Amyl acetate, C10-11rich aromatic hydrocarbons (CAS Reg. No. 64742-94-5), C11-12rich aromatic hydrocarbons (CAS Reg. No. 64742-94-5), C9rich aromatic hydrocarbons (CAS Reg. No. 64742-95-6), Chlorobenzene, Choline chloride (CAS Reg. No. 67-48-1), Cod liver oil, Cyclohexane, Cyclohexanone, Cyclohexanone, Decanamide, N,N-dimethyl (CAS Reg. No. 14433-76-2), Diethylene Glycol (CAS No. 111-46-6), Diethylphthalate, Diisopropyl adipate (CAS Reg. No. 6938-94-9), Dipropylene glycol, d-Limonene (CAS Reg. No. 5989-27-5), Ethyl acetate, Ethyl alcohol, Ethyl esters of fatty acids derived from edible fats and oils, Glycerol mono-, di-, and triacetate, Isobornyl acetate, Isobutane (CAS Reg. No. 75-28-5), Isobutyl alcohol, Isopropyl myristate (CAS Reg. No. 110-27-0), Isopropyl myristate, CAS Reg. No. 110-27-0, Kerosene, U.S.P. reagent, Lactic acid, Lactic acid, 2-ethylhexyl ester (CAS Reg. No. 6283-86-9), Lactic acid, 2-ethylhexyl ester, (2S)-(CAS Reg. No. 186817-80-1), Lactic acid, n-propyl ester, (S); (CAS Reg. No. 53651-69-7), Mesityl oxide, Methyl 5-(dimethylamino)-2-methyl-5-oxopentanoate (1174627-68-9), Methyl alcohol, Methyl esters of fatty acids derived from edible fats and oils, Methyl isobutyl ketone, Methyl isobutyl ketone, Methyl isobutyl ketone, Methylnamyl ketone (CAS Reg. No. 110-43-0), Mineral oil, U.S.P., or conforming to 21 CFR 172.878 or 178.3620(a), (b), Morpholine 4-C6-12Acyl Derivatives (CAS Reg. No. 887947-29-7), n-Butanol (CAS Reg. No. 71-36-3), n-Decyl alcohol (CAS Reg. No. 112-30-1), n-Hexyl alcohol (CAS Reg. No. 111-27-3), N-Methylpyrrolidone (CAS Reg. No. 872-504), n-Octyl alcohol (CAS Reg. No. 111-87-5), n-Propanol, Oleyl alcohol (CAS Reg. No. 143-28-2, Oxo-decyl acetate (CAS reg. No. 108419-33-6), Oxo-heptyl acetate (CAS Reg. No. 90438-79-2), Oxo-hexyl acetate (CAS Reg. No. 88230-35-7), Oxo-nonyl acetate (CAS Reg. No. 108419-34-7), Oxo-octyl acetate (CAS Reg. No. 108419-32-5), Oxo-tridecyl acetate (CAS Reg. No. 108419-35-8), Petroleum hydrocarbons, light odorless conforming to 21 CFR 172.884, Petroleum hydrocarbons, light, odorless, conforming to 21 CFR 172.884 or 178.3650, Petroleum hydrocarbons, synthetic isoparaffinic, conforming to 21 CFR 172.882, Petroleum hydrocarbons, synthetic isoparaffinic, conforming to 21 CFR 172.882 or 178.3530, Phenol, Propylene glycol, Propylene glycol monomethyl ether, Soybean oil-derived fatty acids, Tetrahydrofurfuryl alcohol (THFA) (CAS Reg. No 97-99-4), Toluenesulfonic acid and its ammonium, calcium, magnesium, potassium, sodium, and zinc salts, Triacetin (glyceryl triacetate), Xylene.

In particular embodiments, sovlents that may be useful in conjunction with concentrates and formulations disclosed herein include, without limitation, amyl acetate, ethyl acetate, methyl or ethyl esters of fatty acids derived from edible fats and oils, glycerol mono-, di-, and triacetate, lactic acid, 2-ethylhexyl ester (CAS Reg. No. 6283-86-9), lactic acid, 2-ethylhexyl ester, (2S)-(CAS Reg. No. 186817-80-1), lactic acid, n-propyl ester, (S) (CAS Reg. No. 53651-69-7), methyl isobutyl ketone, decanamide, N,N-dimethyl (CAS Reg. No. 14433-76-2), and N-Methylpyrrolidone, morpholine 4-C6-12Acyl Derivatives (CAS Reg. No. 887947-29-7).

In embodiments, formulations prepared from polar aprotic solvent concentrates may be selected for an operation pH in a range from about 5 to about 10, or in a range from about 6.5 to about 7.5. In general, solvents may be selected for use with methylsulfonyl phenyl ketone herbicides with a water solubility of greater than about 5% and that yield formulations upon dilution with a pH of greater than or equal to about 5. One skilled in the art will appreciate that any active herbicidal ingredient-solvent pairing for generating a dispersible concentrate may be provided based on solubility, and in consideration of any pH dependency on solubility. In particular, amide based solvents may provide good operational capacity for any active ingredient that has a favorable solubility profile above about pH 5.

In embodiments, the dispersible concentrates may further comprise an organic co-solvent selected from the group consisting of ethyl lactate, ethyl hexyl lactate, fatty acid dimethylamide, N,N-dimethyloctanamide, and N,N-dimethyldecanamide. In embodiments, such a co-solvent may serve as a wetting agent.

In embodiments, the methylsulfonylphenyl ketone herbicide comprises one selected from the group consisting of topramezone, isoxaflutole, mesotrione, sulcotrione, tembotrione, and combinations thereof. These compounds share a common structural profile and may exhibit similar solubility-pH dependencies. In embodiments, the methylsulfonylphenyl ketone herbicide is topramezone:

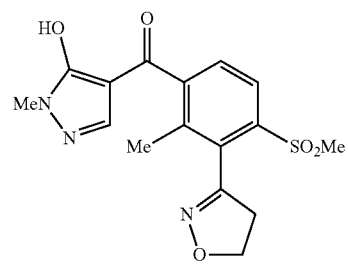

topramezone

Methylsulfonylphenyl ketone herbicides share a structural feature of a central phenyl ring bearing a ketone group and a methanesulfonyl group as in structure I:

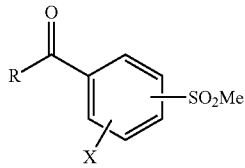

In structure I, X may be $C_1$ to $C_6$ straight chain or branched alkyl, cycloalkyl, halogen, aryl, heteroaryl, trifluoromethyl, nitro, oxo, carboxy, or carboxyalkyl, any of which may be optionally substituted. Optional substitution includes any degree of substitution, such as monosubstitution up to fully-substituted. Optional substituents include, without limitation, fluoro, bromo, chloro, $C_1$ to $C_6$ straight chain or branched alkyl. In particular embodiments, X is any electron withdrawing group as understood by those skilled in the art. That is, any group generally understood to reduce electron density in the phenyl ring to which substituent X is attached. In structure I, R may be any cyclic group, including aryl, heteroaryl, biaryl, cycloalkyl, heterocycloalkyl and the like, any of which may be optionally substituted. In particular embodiments, R is a cyclohexanedione moiety. In embodiments, R may be based on acyclic aliphatic structures as well.

In embodiments, there are provided compounds of structure II:

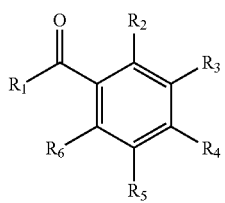

wherein $R_1$ is selected from:

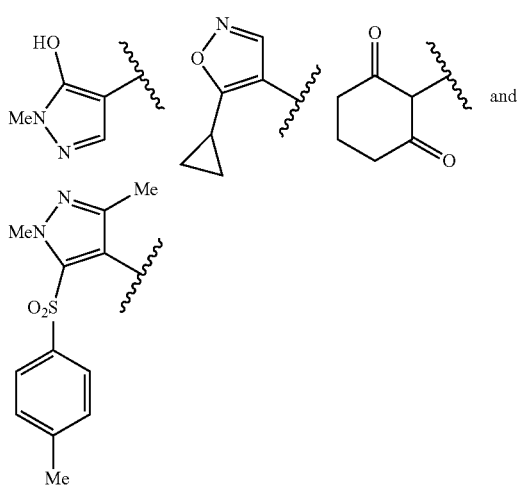

$R_2$ is selected from methyl, nitro, chloro, and methanesulfonyl;

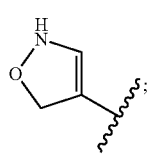 [SMILES: *C1=CNOC1]

$R_3$ is selected from hydrogen, —$CH_2$—O—$CH_2$—$CF_3$, and
$R_4$ is selected from methanesulfonyl, trifluoromethyl, and chloro; and
$R_5$ and $R_6$ are hydrogen.

In embodiments, structure II is topramezone:

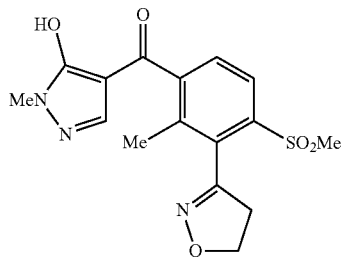 [SMILES: Cc1c(C(=O)c2cnn(C)c2O)ccc(S(C)(=O)=O)c1C1=NOCC1]

In embodiments, structure II is isoxflutole:

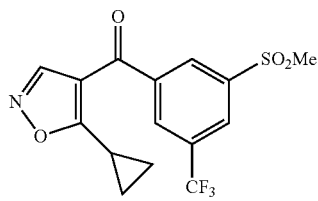 [SMILES: CS(=O)(=O)c1cc(C(=O)c2cnoc2C2CC2)cc(C(F)(F)F)c1]

In embodiments, structure II is mesotrione:

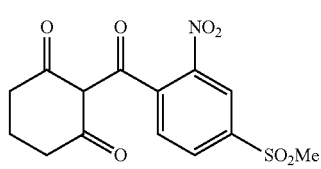

In embodiments, structure II is sulcotrione:

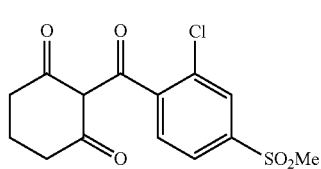 [SMILES: CS(=O)(=O)c1ccc(C(=O)C2C(=O)CCCC2=O)c(Cl)c1]

In embodiments, structure II is tembotrione:

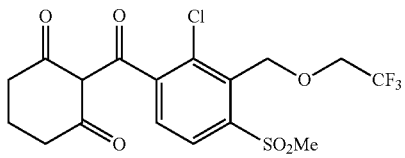 [SMILES: CS(=O)(=O)c1ccc(C(=O)C2C(=O)CCCC2=O)c(Cl)c1COCC(F)(F)F]

In embodiments, the methylsulfonylphenyl ketone herbicide is topramezone and its concentration may be in a range from about 5% to about 25% by weight of the concentrate, or from about 10% to about 20% by weight of the concentrate.

In embodiments, the dispersible concentrate may further comprise a surfactant. In some such embodiments, the surfactant comprises one selected from the group consisting of butyl polyalkylene oxide block copolymers, polyalkylene oxide block copolymers, tristyrylphenol ethoxylates, alkylphenol ethoxylates, castor oil ethoxylates, acetylenic polydiols, organosilicones and mixtures thereof. In embodiments, the surfactant comprises organosilicones. In embodiments, the organosilicones comprise a polyalkyleneoxide modified heptamethyltrisiloxane. In embodiments, the surfactant further comprises an alkyloxypolyethyleneglycol methyl ether. In some such embodiments, the ratio of polyalkyleneoxide modified heptamethyltrisiloxane and allyloxypolyethyleneglycol methyl ether is in a range of from 80:20 to 90:10 percent weight based on the total weight of the concentrate. In embodiments, the surfactant is present in an amount of from about 0.1% to about 15% by weight of the dispersible concentrate.

In embodiments, there are provided dispersible concentrates comprising about 0.1% to about 40% by weight of the concentrate of topramezone and about 0.6% to about 90% by weight of the concentrate of N-methyl pyrrolidone. In particular embodiments, the dispersible concentrate comprises from about 10% to about 20% topramezone. In some embodiments, such concentrates may further comprises an organic co-solvent selected from the group consisting of ethyl lactate, ethyl hexyl lactate, fatty acid dimethylamide, N,N-dimethyloctanamide, and N,N-dimethyldecanamide. In embodiments, such dispersible concentrates may further comprise a surfactant.

In some embodiments, there are provided formulations comprising a dispersible concentrate and water, the dispersible concentrate comprising about 0.1% to about 40% by weight of the concentrate of a methylsulfonylphenyl ketone herbicide, and about 0.6% to about 90% by weight of the concentrate of N-methyl pyrrolidone, wherein in a ratio of dispersible concentrate to water is in a range from about 1:50 to 1:25,000 by volume, and wherein the formulation is in the form of a colloidal suspension.

In embodiments, the formulation may further comprise an additive selected from the group consisting of a surfactant, urea-ammonium nitrate (UAN), and combinations thereof. In embodiments, the formulation may comprise a methylsulfonylphenyl ketone herbicide comprising tompramezone. In some embodiments, topramezone is present in a range from about 10% to about 20% by weight of the concentrate. In embodiments, the dispersible concentrate further comprises an organic co-solvent selected from the group consisting of ethyl lactate, ethyl hexyl lactate, fatty acid dimethylamide, N,N-dimethyloctanamide, and N,N-dimethyldecanamide.

In embodiments, there are provided methods of treating weeds comprising applying to the weeds an herbicidally effective amount of a formulation comprising a dispersible concentrate and water, the dispersible concentrate comprising about 0.1% to about 40% by weight of the concentrate of a methylsulfonylphenyl ketone herbicide, and about 0.6% to about 90% by weight of the concentrate of N-methyl pyrrolidone, wherein in a ratio of dispersible concentrate to water is in a range from about 1:50 to 1:25,000 by volume, and wherein the formulation is in the form of a colloidal suspension.

In embodiments, methods disclosed herein may be used against weeds that are monocots or dicots. In embodiments, the weeds are resistant to glyphosate. In embodiments, methods disclosed herein may employ a methylsulfonylphenyl ketone herbicide comprising topramezone in a concentration in a range from about 10% by weight of the concentrate to about 20% by weight of the concentrate. In embodiments, such formulations may further comprise an additive selected from the group consisting of a surfactant, urea-ammonium nitrate (UAN), and combinations thereof.

Embodiments disclosed herein relate to a dispersible concentrate (DC) composition comprising from about 0.1% to about 40% by weight of topramezone and from about 0.6% to about 90% by weight of a solvent, wherein the solvent has water solubility of between about 0.1% and about 100%, and wherein the weight percentages are based on the total weight of the composition.

Embodiments disclosed herein provide a dispersible concentrate which forms a liquid-suspension of topramezone particles upon dilution with water. The particles are of sufficiently small size to facilitate rapid dissolution and improve application in the field to control weeds while reducing the amount of topramezone employed.

In one aspect, embodiments disclosed herein provide methods of preparing readily-solubilized dispersions of topramezone comprising diluting the dispersible concentrate compositions disclosed herein in water at a ratio from about 1:50 to about 1:25000 (composition:water) by volume, or from about 1:200 to about 1:5000 by volume.

In one aspect, embodiments disclosed herein provide a method for increasing the herbicidal efficacy of a liquid-dispersion of topramezone for a crop, comprising preparing a formulation comprising an effective amount of topramezone.

In one aspect, embodiments disclosed herein also provide a formulation comprising a. from about 0.00004% to about 0.8% by weight of topramezone; b. from about 0.0008% to about 1.5% by weight of a solvent, wherein the solvent has water solubility of between about 0.1% and about 100%; c. from about 95% to about 99.999% by weight of water, and; d. optionally a surfactant from about 0.00001% to about 0.35%, wherein the weight percentages are based on the total weight of the composition.

In another aspect, embodiments disclosed herein provide methods of controlling weeds, such as monocot and dicot weeds. In certain embodiments, the method includes applying a formulation prepared from the DC composition to a crop plant in need of weed control or at risk of undesirable weeds.

Embodiments disclosed herein provide a dispersible concentrate (DC) composition comprising from about 0.1% to about 40%, by weight of topramezone [3-(4,5-dihydro-1,2-oxazol-3-yl)-4-mes yl-o-tolyl](5-hydroxy-1-methyl-1H-pyrazole-4-yl)methanone and from about 0.6% to about 90% by weight of a solvent, wherein the solvent has water solubility of between about 0.1% and about 100%, and wherein the weight percentages are based on the total weight of the composition.

In certain embodiments, the dispersible concentration includes topramezone in the amount of from about 0.1% to about 40%, from about 10% to about 20% or from about 14% to about 18% by weight based on the total weight of the composition.

In certain embodiments, the dispersible concentration includes a solvent in the amount of from about 0.6% to about 90%, from about 30% to about 90%, from about 60% to about 90% or from about 75% to about 85% by weight based on the total weight of the composition.

Solvents that are suitable for use in the DC compositions include, but not limited to, N-methyl pyrrolidone, ethyl lactate, ethyl hexyl lactate, fatty acid dimethylamide, N,N-dimethyloctanamide, N,N-dimethyldecanamide, and a blend or mixtures thereof. In certain embodiments, the solvent does not include water, thus, providing a non-aqueous DC composition. In such embodiments, it will be understood that a certain amount of water may be present due to normal exposure to the environment and thus, the compositions should not be considered limited to be strictly anhydrous, although such anhydrous preparations can be made and are within the scope of the compositions disclosed herein. In certain embodiments, the solvent does not include aliphatic alcohol ethoxylates.

As used herein, the term "surfactant" encompasses a blend of surfactants. The DC compositions may exhibit surprisingly good dispersion properties, good herbicidal efficacy, and reduced herbicide use compared to other commonly used formulation types.

In certain embodiments, the solvent in the composition comprises N-methyl pyrrolidone, ethyl lactate, ethyl hexyl lactate, fatty acid dimethylamide, N,N-dimethyloctanamide, N,N-dimethyldecanamide, or mixtures thereof (i.e., blends of two or more solvents).

The water solubility of the solvent in the DC composition may be in a range from about 0.1% to infinitely miscible based on the total weight of the concentrate. When two or more solvents are present in the DC composition, the water solubility may be calculated based on the combined effect of the solvent mixtures.

The DC compositions may further comprise a surfactant. The surfactant may include a butyl polyalkylene oxide block copolymers, polyalkylene oxide block copolymers, tristyrylphenol ethoxylates, alkylphenol ethoxylates, castor oil ethoxylates, acetylenic polydiols, organosilicones, or mixtures thereof. In certain embodiments, the surfactant includes organosilicones. In further embodiments, the surfactant includes a polyalkyleneoxide modified heptamethyltrisiloxane. In yet further embodiments, the surfactant comprises an allyloxypolyethyleneglycol methyl ether. In certain embodiments, the ratio of polyalkyleneoxide modified heptamethyltrisiloxane to allyloxypolyethyleneglycol methyl ether may be in a range of from 80:20 to 90:10 percent weight based on the total weight of the compostion. In a specific embodiment, the surfactant includes Silwet L-77®.

The amount of surfactant in the DC compositions may be from about 0.1% to about 15% by weight of the composition; or from about 5% to about 15% by weight based on the total weight of the composition.

Embodiments disclosed herein also provide a method of forming a liquid-suspension of topramezone by dilution of a DC composition in a ratio from about 1:50 to about 1:25000 (DC:water), or in a ratio from about 1:200 to about 1:5000 by volume with water.

Embodiments disclosed herein provide formulations prepared from the DC compositions disclosed herein.

The formulation disclosed herein may include: a. from about 0.00004% to about 0.8% by weight of topramezone; b. from about 0.0008% to about 1.5% by weight of a solvent, wherein the solvent has water solubility of from about 0.1% and about 100%; c. from about 95% to about 99.999% by weight of water, and; d. optionally a surfactant from about 0.00001% to about 0.35%, wherein the weight percentages are based on the total weight of the formulation.

In certain embodiments, the formulation includes from about 0.0008% to about 4.0% by weight of a solvent based on the total weight of the formulation.

In certain embodiments, the formulation includes from about 96.9% to about 99.99% by weight of water based on the total weight of the formulation.

Formulations disclosed herein can be produced by mixing or suspending topramezone, optionally an adjuvant, optionally a stabilizer, and a diluent or a solvent.

It is well within a skill of the art to prepare such formulations using well-known techniques, such as dilutions. The dilutions may be made in water. The dilutions may be made by adding water to the DC composition at a ratio from about 1:50 to about 1:25000 (DC:water) or at a ratio from about 1:200 to about 1:5000) by volume. In general, ratios of dilution varies depending upon the concentration of the active ingredient (e.g., topramezone) in the DC composition in which a plant is being treated, the intensity of the weed infestation, weather conditions, the predominant infesting weed species, and other factors, and may be readily determined by established biological tests known to those skilled in the art.

Embodiments relate to methods of treating weeds comprising applying a herbicidally effective amount of the formulations disclosed herein. A person skilled in the art would readily know how to "treat" weeds, as these techniques are well known in the art and are applicable to the compositions disclosed herein. Therefore, embodiments disclosed herein provide methods for controlling weeds. In one embodiment, a method includes applying (contacting) a formulation comprising a. from about 0.00004% to about 0.8% by weight of 3-(4,5-dihydro-1,2-oxazol-3-yl)-4-mesyl-o-tolyl](5-hydroxy-1-methyl-1H-pyrazole-4-yl; b. from about 0.0008% to about 1.5% by weight of a solvent, wherein the solvent has water solubility of between about 0.1% and about 100%; c. from about 95% to about 99.999% by weight of water, and; d. optionally a surfactant from about 0.00001% to about 0.35%, wherein the weight percentages are based on the total weight of the composition, to a weed, a crop or a plant habitat or area. Such methods are applicable to a plant including, but not limited to, one or more weeds described herein.

The phrase "herbicidally effective amount" of the formulation means a sufficient amount of the formulation to provide the desired effect. In general, the formulation is employed in amounts that do not cause phytotoxic damage to any part of the crop but still effectively controls the weeds threatening the crop. The amount of the formulation may vary depending on specific crops and other factors. It is well within an ordinary skill in the art to determine the necessary amount of the formulation. A crop for the purpose of embodiments disclosed herein refers but is not limited to a useful agricultural commodity such as cornfield corn, seed corn, or sweet corn. Crops can be transgenic or non-transgenic.

The formulations disclosed herein may be used against weeds including monocot and dicot weeds. Non-limiting examples of weeds include, *Amaranthus*, Burcucumber, Carpetweed, Chickweed, Cocklebur, Dandelion, Horseweed, Kochia, Lambsquarters, Nightshade, Pigweed, Ragweed, Smartweed, Thistle, Velvetleaf, Waterhemp, Foxtails, Barnyardgrass and others. In certain embodiments, the weeds are glyphosate resistant weeds, amino lactate synthase resistant weeds, triazine resistant weeds, HPPD (enzyme 4-hydroxyphenyl pyruvate dioxygenase) resistant wees and the like.

In another embodiment, the formulation can be applied to soil, pre and post planting and to growing crops as a spray.

As used herein, the singular forms "a", "and," and "the" include plural referents unless the context clearly indicates otherwise As used herein, all numerical values relating to amounts, weights, and the like, are defined as "about" or "approximately" each particular value, namely, plus or minus 10%. For example, the phrase "at least 5% by weight" is to be understood as "at least 4.5% to 5.5% by weight." Therefore, amounts within 10% of the claimed value are encompassed by the scope of the claims.

For a clearer understanding of the embodiments disclosed herein, specific examples are set forth below. These examples are merely illustrations and are not to be understood as limiting the scope and underlying principles of the various embodiments in any way. Indeed, various modifications of the various embodiments in addition to those shown and described herein will become apparent to those skilled in the art from the following examples and foregoing description. Such modifications are also intended to fall within the scope of the appended claims.

EXAMPLES

Materials: Agnique KE 3658 is a fatty acid dimethylamide solvent available from Cognis USA, Cincinnati, Ohio 45232. Agsolexl is N-methyl-2-pyrrolidone, a solvent supplied by Ashland Corporation. Purasolv EL is Ethyl Lactate, a solvent supplied by Purac America, Inc. Purasolv EHL is Ethyl Hexyl Lactate, a solvent supplied by Purac America, Inc. Halcomid M8-10 is a fatty acid dimethylamide solvent available from Stepan Company, Northfield, Ill. 60093. Silwet L-77® is a mixture of polyalkeleneoxide modified heptamethyltrisiloxane and allyloxypolyethyleneglycol methyl ester and is a surfactant supplied by GE silicones. Surfynol 465 is an acetylenic polydiol surfactant supplied by Air Products. Emulpon CO-360 is a castor oil ethoxylate non-ionic surfactant available from Akzo Nobel Surfactants, Chicago, Ill. 60607. Makon TSP 16 is a tristyrylphenol ethoxylate non-ionic surfactant from available from the Stepan Co., Northfield, Ill. 60093. Stepfac TSP-PE is a tristyrylphenol ethoxylate phosphate ester anionic surfactant and is available from the Stepan Co., Northfield, Ill. 60093. Soprophor BSU is a tristyrylphenol ethoxylate non-ionic surfactant and is available from Rhodia, Cranbury, N.J. 08512. Soprophor 3D33 is a tristyrylphenol ethoxylate phosphate ester anionic surfactant such as 2,4,6-tris(1-phenylethyl)polyoxyethylene phosphate and is available from Rhodia, Cranbury, N.J. 08512. Toximul 8320 is a butyl polyalkylene oxide block copolymer non-ionic surfactant available from the Stepan Co., Northfield, Ill. 60093. As used herein, "topramezone technical" contains 97-100% by weight topramezone.

Example 1

A formulation was prepared by conventional blending techniques consisting of topramezone technical at about 15% by weight, an amide solvent Agnique KE 3658 at about 10% by weight, N-methyl-2-pyrrolidone solvent at about 75%, wherein the weight percentages are based on the total weight of the composition. The Topramezone technical was first dissolved into N-methyl-2-pyrrolidone. Then, Agnique KE 3658 was added. The mixture was then blended until a clear homogeneous solution was obtained. The formulation had good dispersion properties forming a readily-solubilized suspension of topramezone particles upon dilution with water.

Example 2

A formulation was prepared by conventional blending techniques consisting of topramezone technical at about 12% by weight, a surfactant Silwet L-77® at about 16% by weight, an amide solvent, like Halcomid M-8-10, at about 10% by weight, a solvent N-methyl-2-pyrrolidone at about 62% by weight, wherein the weight percentages are based on the total weight of the composition. The Topramezone technical was first dissolved into a blend of Halcomid M-8-10 and N-methyl-2-pyrrolidone. Then, Silwet L-77® was added. The mixture was then blended until a clear homogeneous solution was obtained. The formulation had good dispersion properties forming a readily-solubilized suspension of topramezone particles upon dilution with water.

Example 3

A formulation was prepared by conventional blending techniques consisting of topramezone technical at about 3% by weight, a surfactant Toximul 8320 at about 12% by weight, a solvent Purasolv EL at about 85% by weight, wherein the weight percentages are based on the total weight of the composition. The Topramezone technical was first dissolved into Purasolv EL. Then, Toximul 8320 was added. The mixture was then blended until a clear homogeneous solution was obtained. The formulation had good dispersion properties forming a readily-solubilized suspension of topramezone particles upon dilution with water.

Example 4

A formulation was prepared by conventional blending techniques consisting of topramezone technical at about 17% by weight, a solvent N-methyl-2-pyrrolidone at about 83% by weight, wherein the weight percentages are based on the total weight of the composition. The topramezone technical was dissolved into N-methyl-2-pyrrolidone. The mixture was then blended until a clear homogeneous solution was obtained. The formulation had good dispersion properties forming a readily-solubilized suspension of topramezone particles upon dilution with water and is expected to have good biological efficacy.

Example 5

A formulation was prepared by conventional blending techniques consisting of topramezone technical at about 2% by weight, a surfactant Surfynol 465 at about 15% by weight, a solvent ethyl hexyl lactate at about 83% by weight, wherein the weight percentages are based on the total weight of the composition. The Topramezone technical was first dissolved into the ethyl hexyl lactate. Then, Surfynol 465 added. The mixture was then blended until a clear homogeneous solution was obtained. The formulation had good dispersion properties forming a readily-solubilized suspension of topramezone particles upon dilution with water.

Example 6

A formulation was prepared by conventional blending techniques consisting of topramezone technical at about 10% by weight, a surfactant Emulpon C0-360 at about 14% by weight, and a solvent N-methyl-2-pyrrolidone at about 76% by weight, wherein the weight percentages are based on the total weight of the composition. The topramezone technical was first dissolved into N-methyl-2-pyrrolidone. Then, EmulponCO-360 was added. The mixture was then blended until a clear homogeneous solution was obtained. The formulation had good dispersion properties forming a readily-solubilized suspension of topramezone particles upon dilution with water.

Example 7

This Example shows stability tests performed on exemplary dispersible concentrates.

Dispersible concentrates were prepared in triplicate and the tested for stability which is summarized in Table 1 below. Concentrates A, B, and C were prepared by dissolution of about 15% by weight of the concentrate of topramezone technical in N-methyl pyrrolidone.

TABLE 1

| Test | Concentrate A | | | Concentrate B | | | Concentrate C | | |
| --- | --- | --- | --- | --- | --- | --- | --- | --- | --- |
| | Initial | 2 weeks 20° C. | 2 weeks 54° C. | Initial | 2 weeks 20° C. | 2 weeks 54° C. | Initial | 2 weeks 20° C. | 2 weeks 54° C. |
| Assay (% w/w) | 15.0 | 15.0 | 15.1 | 14.8 | 14.7 | 14.9 | 14.8 | 14.8 | 15.0 |
| pH (1% dilution in DI water) | 6.5 | 6.4 | 6.2 | 6.4 | 6.4 | 6.1 | 6.5 | 6.3 | 6.2 |
| Suspensibility in 342 ppm water | 100 | 100 | 100 | 100 | 100 | 100 | 100 | 100 | 100 |

The concentrates exhibited excellent stability after two weeks at 20° C. and at 54° C., the latter temperature being considered by the EPA and the EU to be equivalent to one year stability. By contrast, the suspension concentrates (coarse dispersion) employed in the art are inherently thermodynamically unstable as they tend to settle, form a supernatant layer with time and are prone to viscosity changes as well as particle size growth. The dispersible concentrates disclosed herein are not susceptible in this manner.

Example 8

This Example shows test DC Formulations A, B, and C diluted with water and applied against various weeds with effectiveness compared against a standard suspension (coarse dispersion) formulation. The preparation of DC Formulation A, B, and C (Table 2) was accomplished by dissolving technical grade topramezone in N-methyl pyrrolidone and then adding the wetting/penetrating agent. The final solutions were translucent golden in color.

TABLE 2

| Ingredients | Formula A | Formula B | Formula C |
| --- | --- | --- | --- |
| N-methyl pyrrolidone | 73.2 | 73.2 | 73.2 |
| Topramezone technical | 15 | 15 | 15 |
| Silwet L-77 | 11.8 | 0 | 5.9 |
| Ethyl lactate | 0 | 11.8 | 5.9 |
| Total | 100 | 100 | 100 |

These experimental formulations were compared to the current standard commercial formulation of topramezone designated as a 2.8 pound active ingredient per gallon Suspension Concentrate (2.8 SC). Formulations tested in the field were constructed as 1.29 pound per gallon Dispersible Concentrate (1.29 DC). All field trial testing compared the standard formulation with the experimental formulations at the same rate of active ingredient per acre.

In all locations, trials were conducted throughout the corn growing region and constructed in typical small-plot fashion with each treatment replicated 3 or 4 times. Individual plots ranged from 6 to 12 feet wide and approximately 20 to 30 feet in length. All plots included 2 to 4 rows of corn. Applications were made with a $CO_2$ hand-held sprayer to simulate commercial applications. Application water volumes ranged from approximately 10 to 20 gallons per acre. All applications were made post-emergence to the crop and weeds. Weed height at application generally ranged from 2 to 8 inches at the time of application. Various native weeds were tested at each location and the broad spectrum of weeds included are representative of the weed flora throughout the global cultivated corn growing region. Evaluation of weed control activity was made visually and recorded as an estimated percent control based on the untreated control plots in each trial. A summary of test weeds are shown in Table 3 below.

TABLE 3

| Scientific Name | Common Name |
| --- | --- |
| *Abutilon theophrasti* | Velvetleaf |
| *Amaranthus palmerii* | Palmer amaranth |
| *Amaranthus* sp. | Pigweed species |
| *Ambrosia artemisiifolia* | Common ragweed |
| *Brachiaria platyphylla* | Broadleaf signalgrass |
| *Chenopodium album* | Lambsquarters |
| *Hibiscus trionium* | Venice mallow |
| *Ipomoea* sp. | Morningglories |
| *Portulaca oleracea* | Purslane |
| *Setaria faberii* | Giant foxtail |
| *Setaria glauca* | Yellow foxtail |

Several trials on different weed species were performed at standard application rates of herbicide. Results are summarized in Table 4 below.

TABLE 4

| Treatment | Formulation pounds active ingredient/gal | Formulation Type | Rate pounds active ingredient/acre | Weed Species, Location, Percent Control | | | | | |
|---|---|---|---|---|---|---|---|---|---|
| | | | | Amaranthus sp. Springflied, NE | Chenopodium album Springfield, NE | Amaranthus sp. Springfield, NE | Setaria glauca Phelps, NY | Amaranthus retroflexus Ft. Collins, CO | Amaranthus palmerii Stoneville, MS |
| Topramezone Commercial | 2.8 | SC | 0.016 | 71 | 99 | 64 | 57 | 65 | 93 |
| Topramezone Experimental 'A' | 1.29 | DC | 0.016 | 87 | 100 | 88 | 80 | 98 | 100 |
| Topramezone Experimental 'B' | 1.29 | DC | 0.016 | 90 | 99 | 89 | 70 | 93 | 100 |
| Topramezone Experimental 'C' | 1.29 | DC | 0.016 | 86 | 100 | 93 | 76 | 100 | 98 |

Table 4 shows results from four locations on five different weed species. The standard commercial product, listed as "Topramezone Commercial" provided 71 to 99 percent control across weed species and locations vs. 70 to 100 percent control for the experimental formulations. All products were used at the same rate per acre of 0.016 pounds of active ingredient. In almost every case, the experimental formulations provided better control than the Topramezone Commercial standard. Typically, depending on cropping system, weed type and density, less than 75 percent control in unacceptable in crop production and will not allow achievement of maximum crop yields. Control of 75-85 percent is considered good and 86-100% is considered excellent.

Trials were also run at marginal application rates to expose differences in treatments. The results are shown in Table 5 below.

TABLE 5

| Treatment | Formulation concentration (pounds active ingredient/gallon) | Formulation Type | Rate per acre (pounds active ingredient) | Weed Species, Location, Percent Control | | | |
|---|---|---|---|---|---|---|---|
| | | | | Abutilon theophrasti | Amaranthus sp. Springfield, NE | Chenopodium album | Setaria faberii |
| Topramezone Commercial | 2.8 | SC | 0.011 | 10 | 10 | 10 | 10 |
| Topramezone Experimental 'A' | 1.29 | DC | 0.011 | 40 | 67 | 50 | 30 |
| Topramezone Experimental 'C' | 1.29 | DC | 0.011 | 37 | 60 | 40 | 20 |

Table 5 shows results of trials conducted on four weeds with the commercial formulation and experimental formulations of topramezone applied at the low end of the labeled rate (0.011 pounds of active ingredient per acre, which can be used for certain weeds or in certain mixtures of herbicides). At this commercial rate the standard formulation provided only 10% control of the four weeds tested while the experimental formulations provided from 2 to 6.7 times greater activity (20 to 67 percent control). Certain weeds, such as Chenopodium, Abutilon and others are often very difficult to control.

Further trials were run at normal application rates of herbicide without added surfactant. The results are shown in Table 6 below.

TABLE 6

| Treatment | Formulation concentration (pounds active ingredient/gallon) | Formulation Type | Rate per acre (pounds active ingredient) | Weed Species, Location, Percent Control | | | |
|---|---|---|---|---|---|---|---|
| | | | | *Abutilon theophrasti* | *Amaranthus* sp. Springfield, NE | *Chenopodium album* | *Setaria faberii* |
| Topramezone Commercial | 2.8 | SC | 0.016 | 23 | 38 | 33 | 20 |
| Topramezone Experimental 'A' | 1.29 | DC | 0.016 | 63 | 63 | 50 | 27 |
| Topramezone Experimental 'C' | 1.29 | DC | 0.016 | 47 | 53 | 43 | 23 |

Table 6 shows the same weeds at a higher use rate of all formulations and again the experimental formulations provided greater activity in all cases.

Further trials were run at normal application rates of herbicide with normally added surfactants. The results are shown in Table 7 below.

TABLE 7

| Treatment | Formulation concentration (pounds active ingredient/gallon) | Formulation Type | Rate per acre (pounds active ingredient) | Weed Species, Location, Percent Control | | | |
|---|---|---|---|---|---|---|---|
| | | | | *Abutilon theophrasti* | *Amaranthus* sp. Springfield, NE | *Chenopodium album* | *Setaria faberii* |
| Topramezone Commercial | 2.8 | SC | 0.016 + surfactant* | 83 | 80 | 92 | 53 |
| Topramezone Experimental 'A' | 1.29 | DC | 0.016 + surfactant* | 88 | 90 | 98 | 92 |
| Topramezone Experimental 'C' | 1.29 | DC | 0.016 + surfactant* | 85 | 90 | 100 | 83 |

*surfactant = 1% methylated sunflower oil + 2.5% urea ammonium nitrate (28%)

Table 7 shows the same formulations and application rates as Table 5, but with additional surfactants added to the spray mixture. Adjuvants, spreaders, stickers, and the like are standard commercial practice and are often added to enhance activity in specific situations. In the addition of extra surfactants such as methylated sunflower oil (MSO) along with urea ammonium nitrate (UAN), all treatments were improved, but the experimental formulations, in each case were improved to a an overall better level of performance and sometimes significantly better (e.g., *Setaria, Amaranthus*) performance than the standard, commercial formulation.

Further trials were run at normal application rates of herbicide with normally added surfactants. The results are shown in Table 8 below.

TABLE 8

| Treatment | Formulation concentration (pounds active ingredient/gallon) | Formulation Type | Rate per acre (pounds active ingredient) | Weed Species, Location, Percent Control | | | |
|---|---|---|---|---|---|---|---|
| | | | | *Amaranthus retroflexus* | *Amaranthus rudis* | *Hibiscus trionium* Geneva, MN | *Chenopodium album* |
| Topramezone Commercial | 2.8 | SC | 0.016 + surfactant* | 57 | 63 | 70 | 80 |
| Topramezone Experimental 'A' | 1.29 | DC | 0.016 + surfactant* | 87 | 87 | 88 | 88 |

TABLE 8-continued

| Treatment | Formulation concentration (pounds active ingredient/gallon) | Formulation Type | Rate per acre (pounds active ingredient) | Weed Species, Location, Percent Control | | | |
|---|---|---|---|---|---|---|---|
| | | | | Amaranthus retroflexus | Amaranthus rudis | Hibiscus trionium | Chenopodium album |
| | | | | | Geneva, MN | | |
| Topramezone Experimental 'C' | 1.29 | DC | 0.016 + surfactant* | 85 | 85 | 92 | 92 |

*surfactant = 1% methylated sunflower oil + 2.5% urea ammonium nitrate (28%).

Table 8 shows further trials of a commercially used rate of topramezone application with additional surfactants with similar results. The experimental formulations of topramezone indicate significant and consistent advantage over the current commercial formulation often taking 'good' weed control to an 'excellent' category.

The increased activity of the experimental formulations 'A' and 'C' in the presence of additional surfactants/UAN (Table 7 and 8) were particularly unexpected because it was anticipated these conditions would mask the differences between formulations. Further, differences from 80 percent control to 90 percent control and 92 to 98 and 100 percent control (Table 7) allow this product performance to go from 'good' to 'excellent.' In the case of Setaria (Table 7) effective control is improved from 53% to 83-92%, i.e., from 'poor' to 'good' control. Table 8 shows the improvement of topramezone activity from 57% control on Amaranthus retroflexus to 85-87% control, from 63% control on Amaranthus rudis to 85-87%, from 70% on Hibiscus to 88-92% and from 80% on Chenopodium to 88-92%.

What is claimed:

1. A formulation comprising:
a dispersible concentrate and water, the dispersible concentrate comprising:
about 10% to about 20% by weight of the concentrate of topramezone; and
about 0.6% to about 90% by weight of the concentrate of N-methyl pyrrolidone;
wherein topramezone is the only active ingredient of the dispersible concentrate;
wherein a ratio of dispersible concentrate to water is in a range from about 1:50 to 1:25,000 by volume, and wherein the formulation is in the form of a colloidal suspension.

2. The formulation of claim 1, further comprising an additive selected from the group consisting of a surfactant, urea-ammonium nitrate (UAN), and combinations thereof.

3. The formulation of claim 1, wherein a pH of the formulation is in a range from about 5 to about 10.

4. The formulation of claim 3, wherein the pH is in a range from about 6.5 to about 7.5.

5. The formulation of claim 1, wherein the dispersible concentrate further comprises an organic co-solvent selected from the group consisting of ethyl lactate, ethyl hexyl lactate, fatty acid dimethylamide, N,N-dimethyloctanamide, and N,N-dimethyldecanamide.

6. The formulation of claim 1, wherein the dispersible concentrate further comprises a surfactant selected from the group consisting of a butyl polyalkylene oxide block copolymers, polyalkylene oxide block copolymers, tristyrylphenol ethoxylates, alkylphenol ethoxylates, castor oil ethoxylates, acetylenic polydiols, organosilicones, or mixtures thereof.

7. A method of making a colloidal suspension of topramezone comprising:
diluting a dispersible concentrate of topramezone with water, the dispersible concentrate comprising:
about 10% to about 20% by weight of the concentrate of topramezone; and
about 0.6% to about 90% by weight of the concentrate of N-methyl pyrrolidone;
wherein topramezone is the only active ingredient of the dispersible concentrate;
wherein a ratio of dispersible concentrate to water is in a range from about 1:50 to 1:25,000 by volume.

* * * * *